(12) United States Patent
Banchieri et al.

(10) Patent No.: US 7,909,761 B2
(45) Date of Patent: Mar. 22, 2011

(54) ATRAUMATIC TISSUE RETRACTION DEVICE

(75) Inventors: Mike Banchieri, Discover Bay, CA (US); Tamer Ibrahim, Pleasant Hill, CA (US); Raymond Bertolero, Danville, CA (US)

(73) Assignee: Endoscopic Technologies, Inc., San Ramon, CA (US)

( * ) Notice: Subject to any disclaimer, the term of this patent is extended or adjusted under 35 U.S.C. 154(b) by 653 days.

(21) Appl. No.: 11/588,437

(22) Filed: Oct. 26, 2006

(65) Prior Publication Data

US 2008/0103366 A1    May 1, 2008

(51) Int. Cl.
*A61B 1/32* (2006.01)
(52) U.S. Cl. ...................................... 600/208; 600/215
(58) Field of Classification Search ........... 600/201–246
See application file for complete search history.

(56) References Cited

U.S. PATENT DOCUMENTS

| | | | |
|---|---|---|---|
| 4,421,107 A * | 12/1983 | Estes et al. ................ | 600/206 |
| 5,522,791 A | 6/1996 | Leyva | |
| 5,688,223 A | 11/1997 | Rosendahl | |
| 6,142,935 A * | 11/2000 | Flom et al. ................ | 600/206 |
| 6,206,826 B1 | 3/2001 | Mathew et al. | |
| 6,254,534 B1 | 7/2001 | Butler et al. | |
| 6,582,364 B2 | 6/2003 | Butler et al. | |
| 6,814,700 B1 * | 11/2004 | Mueller et al. ............ | 600/206 |
| 6,858,026 B2 * | 2/2005 | Sliwa et al. ............... | 606/28 |

* cited by examiner

*Primary Examiner* — Eduardo C Robert
*Assistant Examiner* — Christina Negrelli
(74) *Attorney, Agent, or Firm* — GSS Law Group; Carol D. Titus; James J. Leary

(57) ABSTRACT

Methods and apparatus for a surgical retractor include a ring, a plurality of flexible straps connected to the ring, a patch of hook or loop material connected to each strap, a coordinating patch of hook or loop material connectable to the patient's skin or the surgical drape. The flexible straps of the surgical retractor may be frangibly connected together. LEDs molded into the distal end create a light source to illuminate the surgical site. The ring may take several forms including a flexible or adjustable ring and an inflatable bladder. The ring of the surgical retractor is inserted into the surgical incision, a patch of loop fastener is attached to the patient, a set of straps connected to the ring are pulled outward and the hook portion is applied to the loop portion to hold the incision open. The retractor is useable for thoracic and other types of surgery.

58 Claims, 8 Drawing Sheets

ATRAUMATIC TISSUE RETRACTION DEVICE

FIELD OF THE INVENTION

The present invention pertains to apparatus and methods for atraumatically retracting tissue. In particular, the present invention creates and maintains an opening through soft tissue.

BACKGROUND OF THE INVENTION

Surgery on the heart is one of the most commonly performed types of surgery that is done in hospitals across the U.S. Cardiac surgery can involve the correction of defects in the valves of the heart, defects to the veins or the arteries of the heart and defects such as aneurysms and thromboses that relate to the circulation of blood from the heart to the body. In the past, most cardiac surgery was performed as open-chest surgery, in which a primary median sternotomy was performed. That procedure involves vertical midline skin incision from just below the super sternal notch to a point one to three centimeters below the tip of the xiphoid. This is followed by scoring the sternum with a cautery, then dividing the sternum down the midline and spreading the sternal edges to expose the area of the heart in the thoracic cavity. This technique causes significant physical trauma to the patient and can require one week of hospital recovery time and up to eight weeks of convalescence. This can be very expensive in terms of hospital costs and disability, to say nothing of the pain to the patient.

Recently, attempts have been made to change such invasive surgery to minimize the trauma to the patient, to allow the patient to recover more rapidly and to minimize the cost involved in the process. New surgical techniques have been developed which are less invasive and traumatic than the standard open-chest surgery. This is generally referred to as minimally-invasive surgery. One of the key aspects of the minimally invasive techniques is the use of a trocar as an entry port for the surgical instruments. In general, minimally invasive surgery entails several steps: (1) at least one, and preferably at least two, intercostal incisions are made to provide an entry position for a trocar; (2) a trocar is inserted through the incision to provide an access channel to the region in which the surgery is to take place, e.g., the thoracic cavity; (3) a videoscope is provided through another access port to image the internal region (e.g., the heart) to be operated on; (4) an instrument is inserted through the trocar channel, and (5) the surgeon performs the indicated surgery using the instruments inserted through the access channel. Prior to steps (1)-(5), the patient may be prepared for surgery by placing him or her on a cardiopulmonary bypass (CPB) system and the appropriate anesthesia, then maintaining the CPB and anesthesia throughout the operation. See U.S. Pat. No. 5,452,733 to Sterman et al. issued Sep. 26, 1995 for a discussion of this technique.

While this procedure has the advantage of being less invasive or traumatic than performing a media, sternotomy, there are numerous disadvantages to using trocars to establish the entry ports for the instruments and viewscope. For example, the trocars are basically "screwed" into position through the intercostal incision. This traumatizes the local tissues and nerve cells surrounding the trocar.

Once in place, the trocar provides a narrow cylindrical channel having a relatively small circular cross-section. This minimizes the movement of the instrument relative to the longitudinal axis and requires specially-designed instruments for the surgeon to perform the desired operation (See, e.g., the Sterman U.S. Pat. No. 5,452,733). In addition, because of the limited movement, the surgeon often has to force the instrument into an angle that moves the trocar and further damages the surrounding tissue and nerves. The need to force the instrument causes the surgeon to lose sensitivity and tactile feedback, thus making the surgery more difficult. The surgical retractor of this invention is designed to reduce the trauma to the patient in providing access to the internal region, to reduce the trauma to the patient during surgery, to provide the surgeon with greater sensitivity and tactile feedback during surgery, and to allow the surgeon to use instruments of a more standard design in performing the non-invasive surgery.

Other less invasive surgical techniques include access to the region of the heart to be corrected by anterior mediastinotomy or a thoracotomy. In a mediastinotomy, an incision is made that is two to three inches in length of a parasternal nature on the left or the right of the patient's sternum according to the cardiac structure that needs the attention in the surgery. Either the third or the fourth costal cartilage is excised depending on the size of the heart. This provides a smaller area of surgical access to the heart that is generally less traumatic to the patient. A thoracotomy is generally begun with an incision in the fourth or fifth intercostal space, i.e. the space between ribs 4 and 5 or ribs 5 and 6. Once an incision is made, it is completed to lay open underlying area by spreading the ribs. A retractor is used to enlarge the space between the ribs.

At the present time, when either of these techniques is used, a retractor is used to keep the ribs and soft tissues apart and expose the area to be operated on to the surgeon who is then able to work in the surgical field to perform the operation.

Major disadvantages of these systems include their limited positioning, complexity, and trauma to the surrounding tissue. It has now been discovered that the shortcomings of the retractors that are known in the prior art can be overcome with a new design as set forth in the following description.

BRIEF SUMMARY OF THE INVENTION

In general, the present invention provides a surgical retractor to allow improved access through a surgical opening through the tissue of a patient. The retractor includes a flexible ring, a plurality of flexible straps connected to the flexible ring, and a connector for attaching the end of the flexible strap to a support surface, such as a patient's skin, a surgical drape and a piece of surgical equipment. The connector may take the form of an adhesive patch on the flexible strap. Alternately, the connector may be a patch of hook or loop material connected to a surface of each of said plurality of straps and a coordinating patch of hook or loop material connectable by adhesive to the support surface.

The diameter of the flexible ring of the surgical retractor may be adjustable. The adjustment of the ring may be achieved with a ratchet mechanism.

One embodiment of the ratchet mechanism is spring loaded and may including: a plurality of openings extending into said flexible ring; an arm having an end sized and configured to extend into said plurality of openings, said arm having an engaged position wherein said end of said arm is located within one of said plurality of openings and a released position wherein said end of said arm is outside all of said plurality of openings; and a spring configured to bias said arm towards said engaged position.

The flexible straps of the surgical retractor may be frangibly connected together. One version of the connection is created by a narrowed portion of the strap material. The straps and sleeve of the surgical retractor are formed of a soft, resilient material, such as silicone material.

The flexible straps of the surgical retractor may be constructed of a soft, resilient material, such as silicone, which provide an atraumatic barrier between the ribs and soft tissues adjacent to the incision site. This reduces the amount of trauma to the ribs and soft tissues caused by various surgical instruments (ie. rib spreaders, surgical tools, etc)

One embodiment of the surgical retractor includes a light source molded into said flexible ring. The light source may take the form of a plurality of LEDs.

In one embodiment, the flexible ring includes an inflatable bladder. A pneumatic line may be attached to said inflatable bladder.

An embodiment of the surgical retractor has a flexible ring that is approximately round.

One embodiment of the surgical retractor includes a malleable flange extending from a distal end thereof.

A method of using a surgical retractor in a surgical incision, includes the steps of: inserting a distal end of the surgical retractor into the surgical incision; causing a ring located on the distal end of the surgical retractor to open to a deployed configuration; placing a plurality of a first part of a coordinating fastener around the surgical incision; pulling a plurality of straps connected with the ring and having a second part of said coordinating fastener such that said second part of said coordinating fastener is connected with said first part of said coordinating fastener.

The method may also include the step of performing a surgical procedure through a passageway extending through the surgical retractor. The surgical procedure may include CABG, valve repair, valve replacement and/or ablation.

One surgical procedure using the surgical retractor is a cardiac ablation procedure. In the procedure two surgical retractors are used in two thoracic incisions located on an opposite side of the sternum.

A method including stretching the straps, thereby providing additional force against tissues forming an edge of the surgical incision.

An embodiment where the parts of the coordinating fastener are hook and loop fastener material and the straps of the surgical retractor are repositioned.

A method includes the step of inflating an inflatable bladder which forms the ring.

A method includes the step of bending outward a malleable flange extending from a distal end of the surgical retractor.

A further method is performed by pulling the straps different amounts to create a non-round passageway.

Yet a further method is performed by pulling the straps approximately the same amount to create a generally round passageway.

The present invention can be used to provide tissue retraction and expand access openings by means of the strength and elastic properties of the materials used to manufacture the retractor. The present invention is also configured to be couplable with an adjustable surgical retractor with blades to be inserted into the patient cavity for large expansion against opposing thoracic structures while providing atraumatic contact with those anatomical structures.

The present invention provides the ability to function to retract tissues, without significant expansion of the incision, but also to enlarge the size of the incision, a function that is provided by the tear strength of the silicone or the ability to combine it with an adjustable surgical blade.

The present invention provides the ability to adjust the tensioning of the straps even after initial deployment through the use of the hook and loop material. This may be necessary when a surgeon needs to enlarge the incision to gain better access to the surgical site. Competitive devices use an adhesive that does not allow for repositioning subsequent to initial deployment.

DETAILED DESCRIPTION OF THE INVENTION

Figure 1:
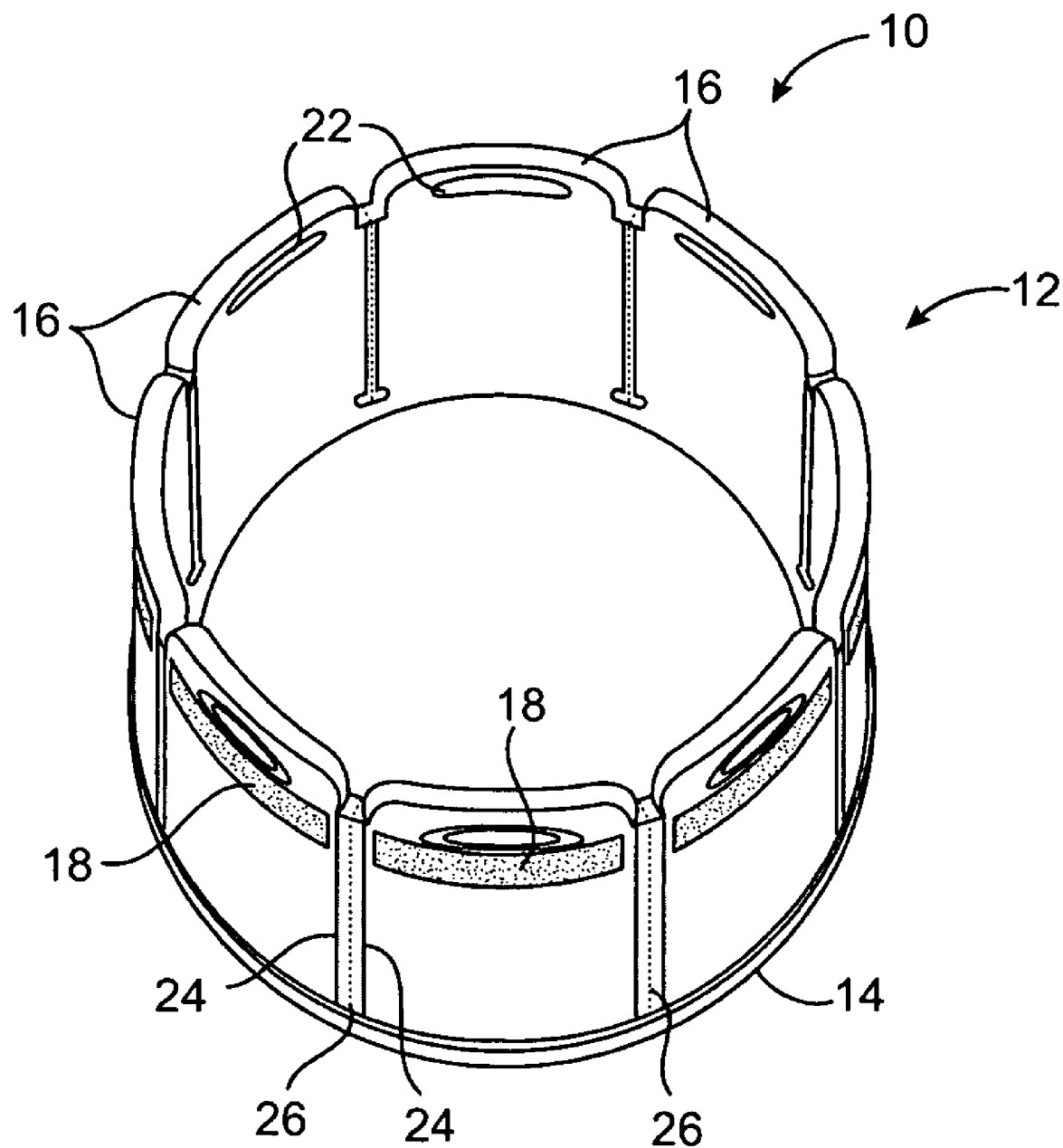
FIG. 1 is a top perspective view of the atraumatic tissue retraction device.

FIG. 1 is a top perspective view of the atraumatic tissue retraction device 10. The atraumatic tissue retractor 10 is a device used to keep the field of view of a thoracotomy, sternotomy, or other surgical portal clear of soft tissues, as well as limit or prevent trauma to the ribs and other soft tissues. The device includes a sleeve 12 with an elastic or flexible ring 14 in the lower or distal end. The ring 14 may be formed of any resilient or elastic material, such as Nitinol, other metals, and plastics. The ring 14 may be adhered, bonded, overmolded into or otherwise connected to the base of the sleeve 12. The sleeve 12 is divided into a multiplicity of straps 16. Any suitable number of straps 16 may be used, preferably from three to twenty, more preferably in the range of four to fourteen and most preferably from six to ten. In the embodiment shown, eight straps 16 are used. Any soft resilient, flexible material may be used to form the sleeve. One suitable material is silicone. Other possible materials include, but are not limited to low durometer polyurethane, nitrile, natural rubber, or low durometer polyvinylchloride.

Figure 2A:
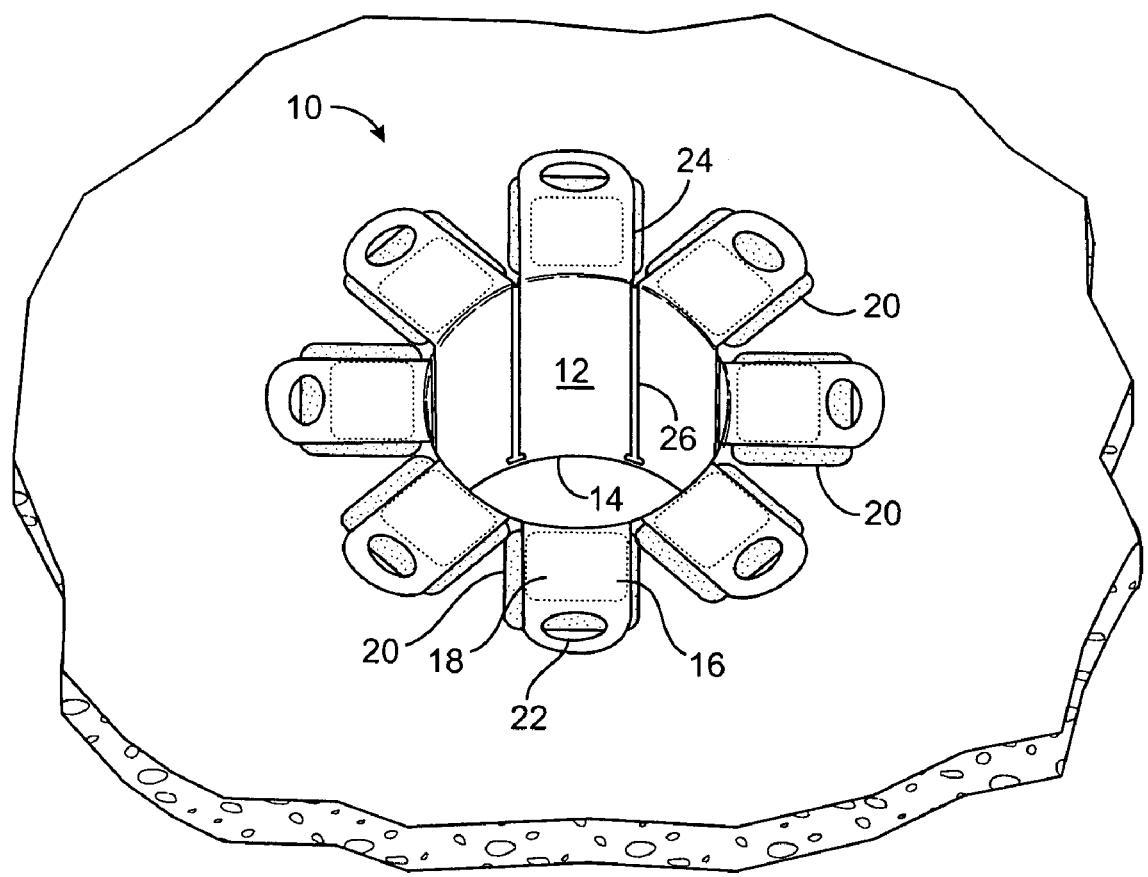
FIG. 2A is a top perspective view of the atraumatic tissue retraction device in use.
Figure 2B:
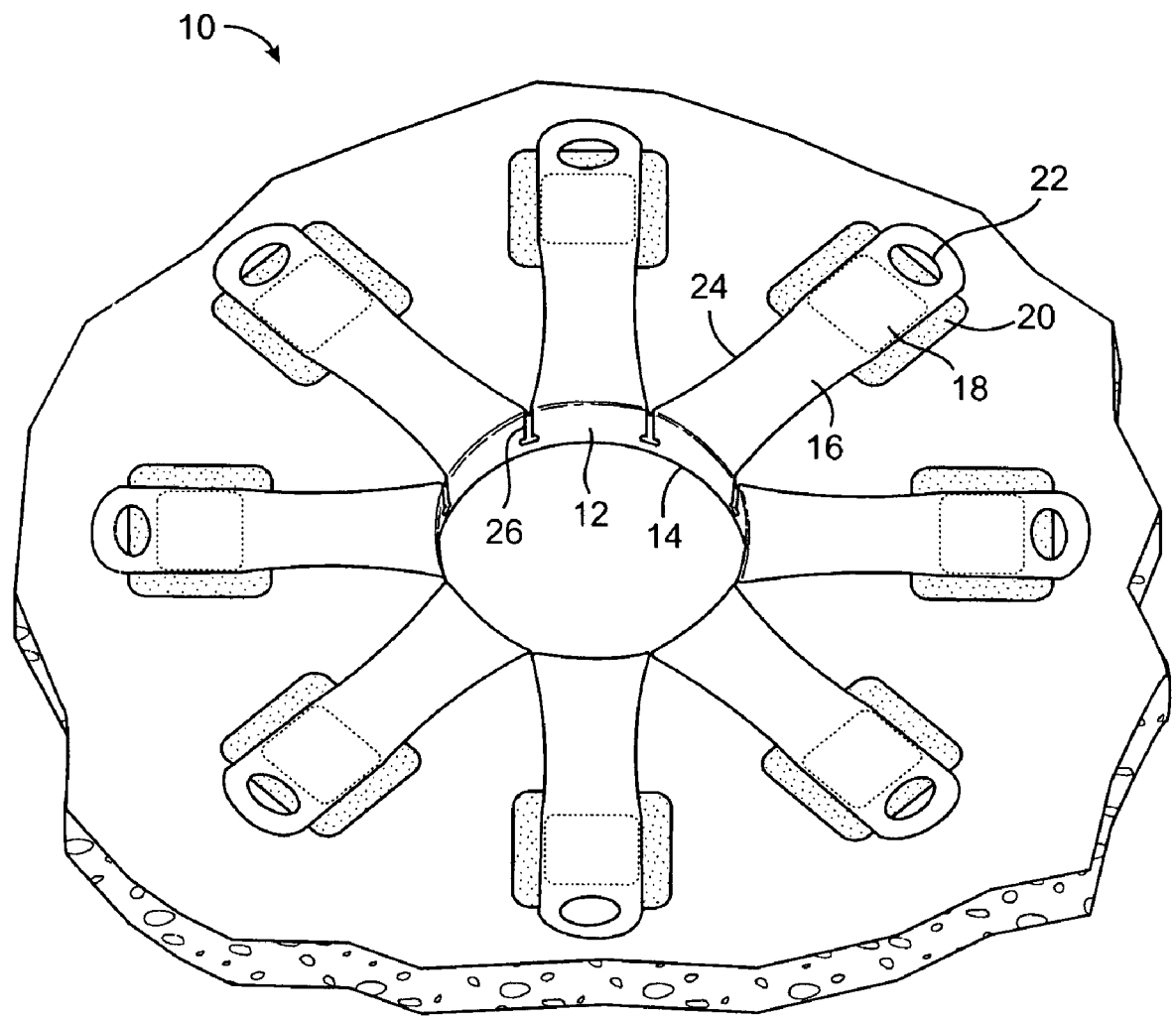
FIG. 2B is a top perspective view of the atraumatic tissue retraction device with the straps extended farther outward.
Figure 3:
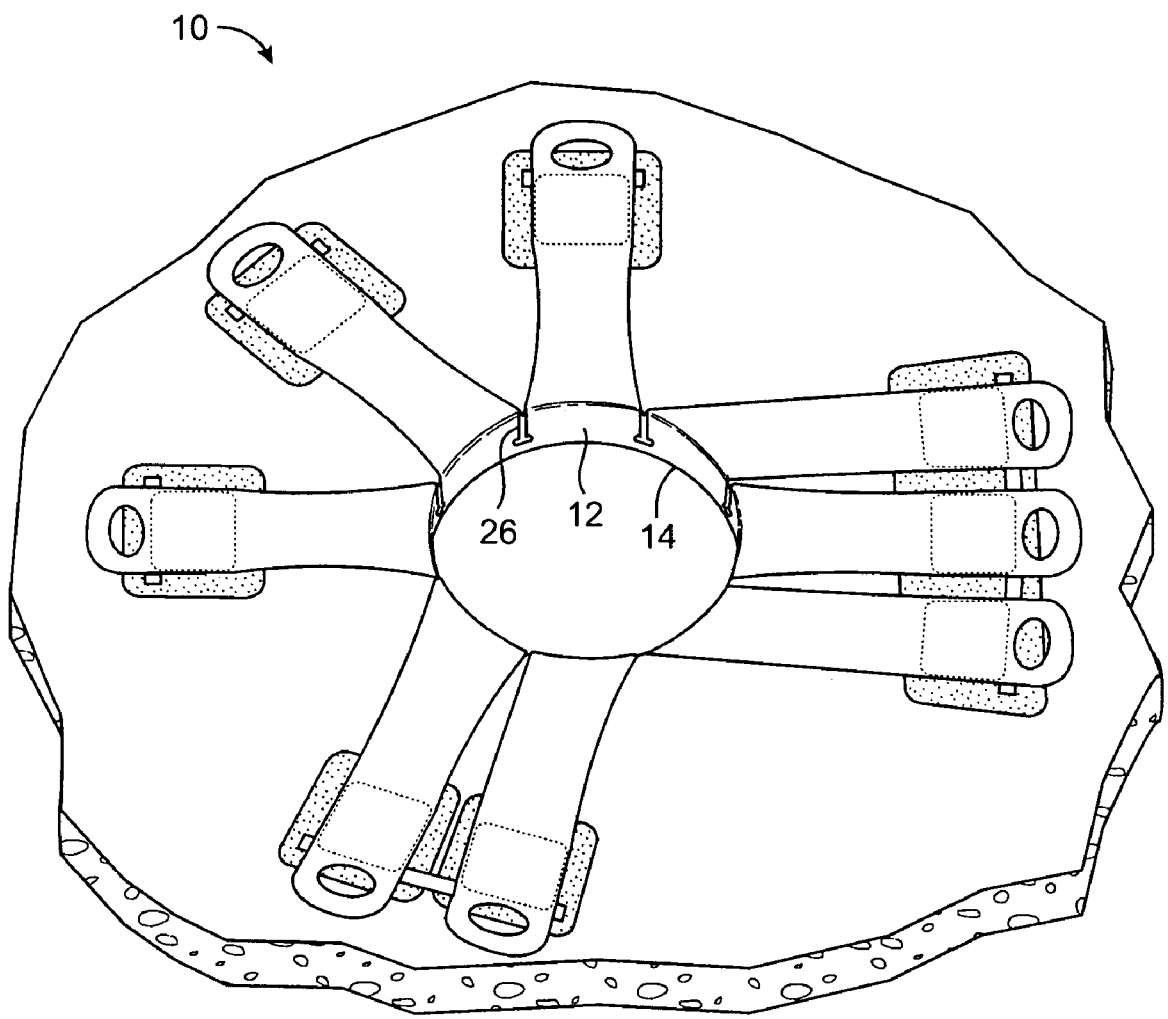
FIG. 3 is a top perspective view of the atraumatic tissue retraction device with the straps extended asymetrically.

A piece of hook or loop material 18 is adhesively bonded or otherwise attached to each strap 16. Included with the device 10 is the coordinating piece of hook or loop material 20 with an adhesive back, as seen in FIGS. 2A, 2B and 3. In the embodiment shown, a set of eight hook pads 18 are adhesively bonded to the straps 16 and eight mating loop pads 20 are attached to the user, the drape or another nearby stable support structure in the surgical field. In the embodiment shown, the straps 16 include holes 22 at the proximal end to allow the user to easily grip the strap 16 and/or hook the strap 16 with an instrument or to a nearby structure.

To use the device 10, the user peels the backing off of the loop pad 20, thereby exposing an adhesive and places it onto the patient's chest, other tissue, surgical drape or other nearly support adjacent to the incision as seen in FIG. 2. The ring 14 of the retractor 10 is then folded or deformed and pushed into the incision. When inserted into the incision, the ring 14 springs back to shape and anchors the distal end of the retractor 10. The eight straps 16 are then pulled away from the incision and adhered to the loop pads 20 via the hook pads 18 to retract the soft tissues. In this manner, the retractor 10 has created and/or maintains an opening and passageway to the surgical site. The distal portion of the straps 16 or the sleeve 12 portion above the ring 14 also protect the tissue from the surgical instruments as they are passed into and out of the passageway.

The present invention is particularly suited for thoracic surgery. In cardiac surgical procedures, the surgical retractor 10 is inserted into at least one incision into the chest to provide access for a surgical procedure, such as CABG, valve repair/replacement and/or ablation procedures. A preferred method is for use in cardiac ablation procedures with one retractor 10 in each one of two thoracic incisions on opposite sides of the sternum. The straps 16 being formed of silicone allow the retractor 10 to provide positive traction to the surrounding tissue and to atraumatically contact and retract the thoracic structures and nerves during any of these procedures.

In use, the surgical retractor 10 has several advantages over typical retractors. The retractor 10 is able to retract tissues, without significant expansion of the incision or to enlarge the size of the incision, if needed. This function is created by the tear strength of the silicone. The versatility of the device 10 is further increased through the use of the hook and loop material. This fastening approach allows for adjustment and re-tensioning of the straps during the procedure.

Figure 7:
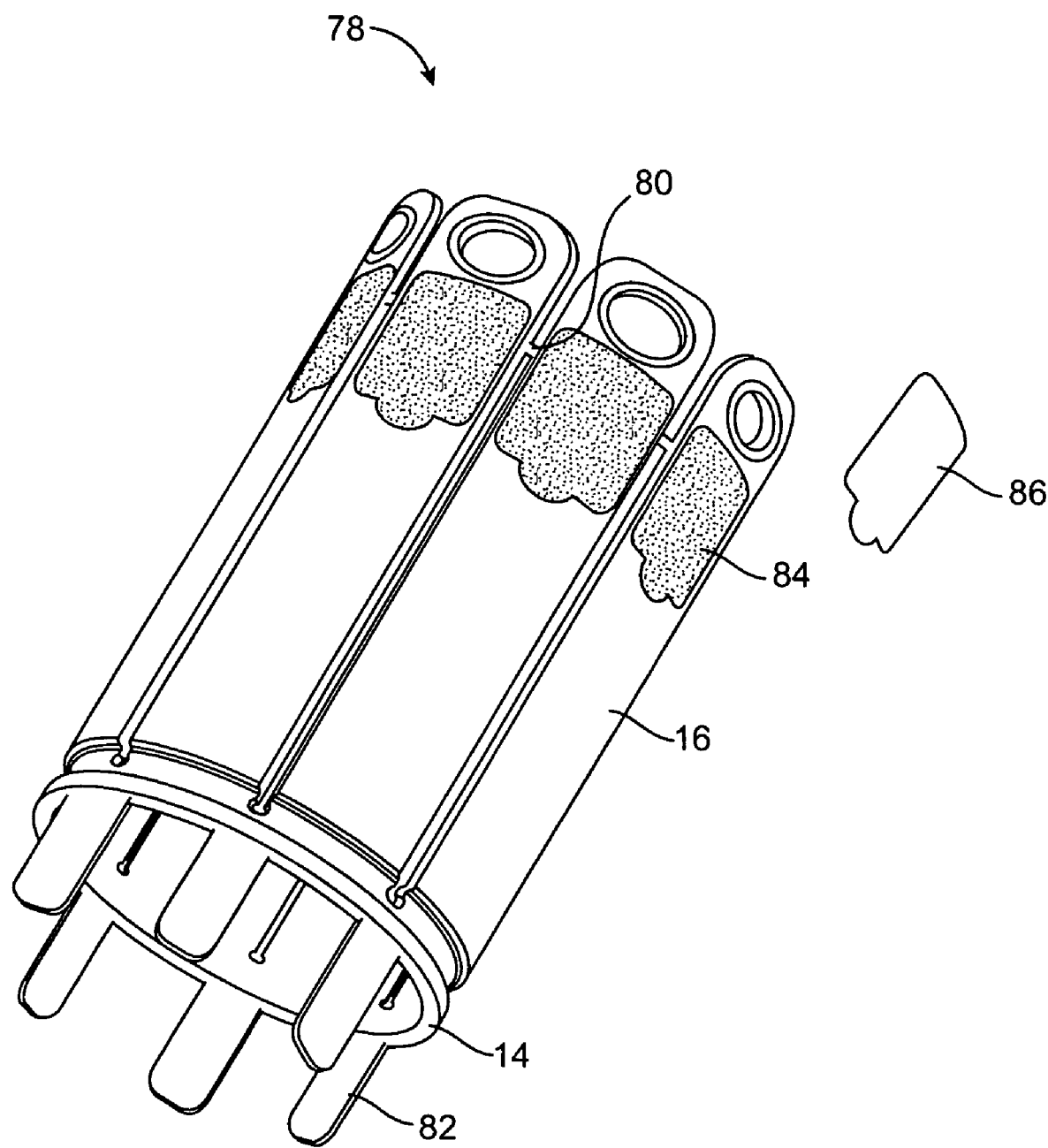
FIG. 7 is a side perspective view of the atraumatic tissue retraction device with flanges extending from the bottom ring.

For ease of use, the straps 16 may be connected along their edges 24 to create the elongated, sleeve 12 structure for initial deployment. The connection 26 between the straps 16 may be formed of a frangible connection 26 that the user may pull apart if desired. In the embodiments shown, the frangible connection 26 is created by molding a narrowed or necked down portion of the strap 16 material. Prior to or during use, the user can easily tear along this weakened portion 26 to separate the strap 16 along as much of the length as desired. FIGS. 2A and 2B show the same embodiment of the retractor 10 in place in a patient in two different configuration. In FIG. 2A, a majority of the length of the straps 16 remains connected along the sides 24. This creates a fairly deep opening for situations where the retractor 10 needs to hold back tissue extending a longer distance into the patient. In FIG. 2B, the straps 16 are pulled out further and separated along most of their lengths. In this version, the retractor 10 is only being used to hold open a comparatively shallow opening. FIG. 7 shows a version of the straps 16 where the straps 16 are connected at the base and at a discrete point 80 near the proximal end of the straps.

Depending on the resilience of the tissue being retracted, the straps 16 may be merely pulled taught and attached to the loop pads 20 as seen in FIG. 2A. Or if additional force is required, the straps 16 may be pulled and stretched, such that the resilience of the straps 16 provides additional retraction force to open and hold open the tissue surrounding the retractor 10, as seen in FIG. 2B. The straps 16 may be overlapped to assure that the tissue being retracted is completely covered by the straps. To accomplish this, the straps 16 may widen as they extend upward from the ring 14.

If desired, only some of the strap may be separated, as seen in FIG. 3. In this embodiment, a thin section near the proximal end of the device is used to connect the straps together. The user then only breaks the frangible connection between the straps for a desired number of straps. In the embodiment shown, a group of two and a group of three straps are left attached together.

Using different tension on the different straps 16 may also allow the user to create a different shaped openings. Such as, stronger tension on two or four (two pair of side-by-side) opposing straps 16 could be used to create an oval or oblong opening. Other effects may be created by varying the relative widths and/or direction of pull of the straps 16. The hook 18 and loop 20 connection also allows the user to independently position, adjust and/or reposition the straps 16 and therefore the retractor 10 during use. If desired, the hook 18 and loop 20 material may also be used as suture stays.

Since the loop pads 20 may be selectively placed as needed, a single size of retractor 10 may be suitable for use for a wide range of size of patient. Further range may be provided by creating additional retractor units 10 of different sizes, including length of straps 16, thickness of straps 16, width of straps 16, diameter of distal ring 14, etc.

Figure 4:
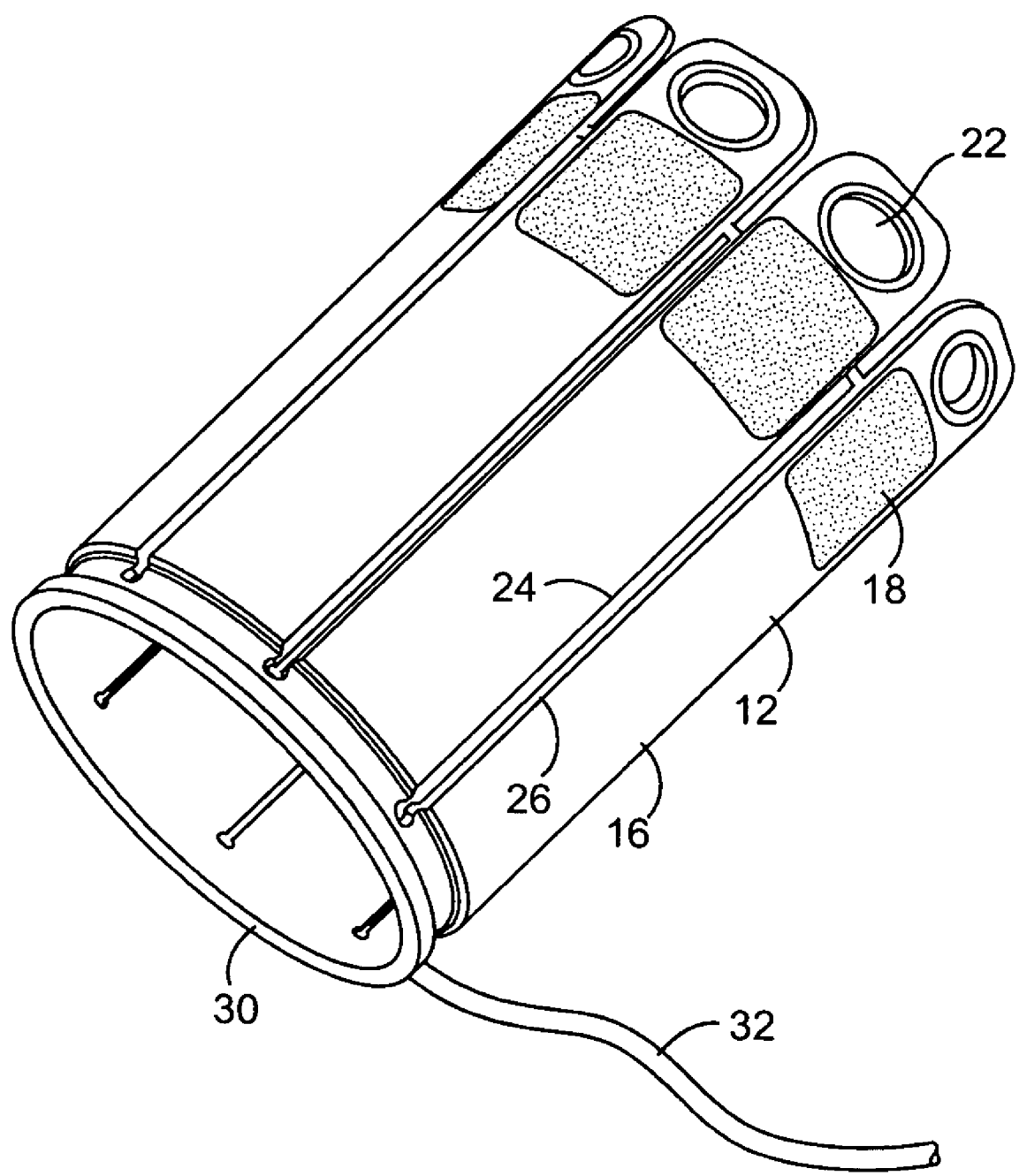
FIG. 4 is a side perspective view of the atraumatic tissue retraction device having an inflatable bladder.

In FIG. 4, the flexible ring 14 at the base of the sleeve 12 is formed of or includes an inflatable bladder 30. A pneumatic line 32 is connected to a source of inflation medium, such as saline or other fluid or gas. The inflation medium source may be in the form of a syringe or a pump that injects the inflation medium into the inflatable bladder 30 and thereby holds the retractor 10 in place. Preferably the system has a mechanism, such as a stopcock or other standard sealing mechanism, to temporarily seal the proximal end of the pneumatic line 32 to maintain the inflation of the bladder 30, while the retractor 10 is in use. Once the procedure is complete, the user can unseal the system and withdraw the inflation medium through the pneumatic line 32.

Figure 5:
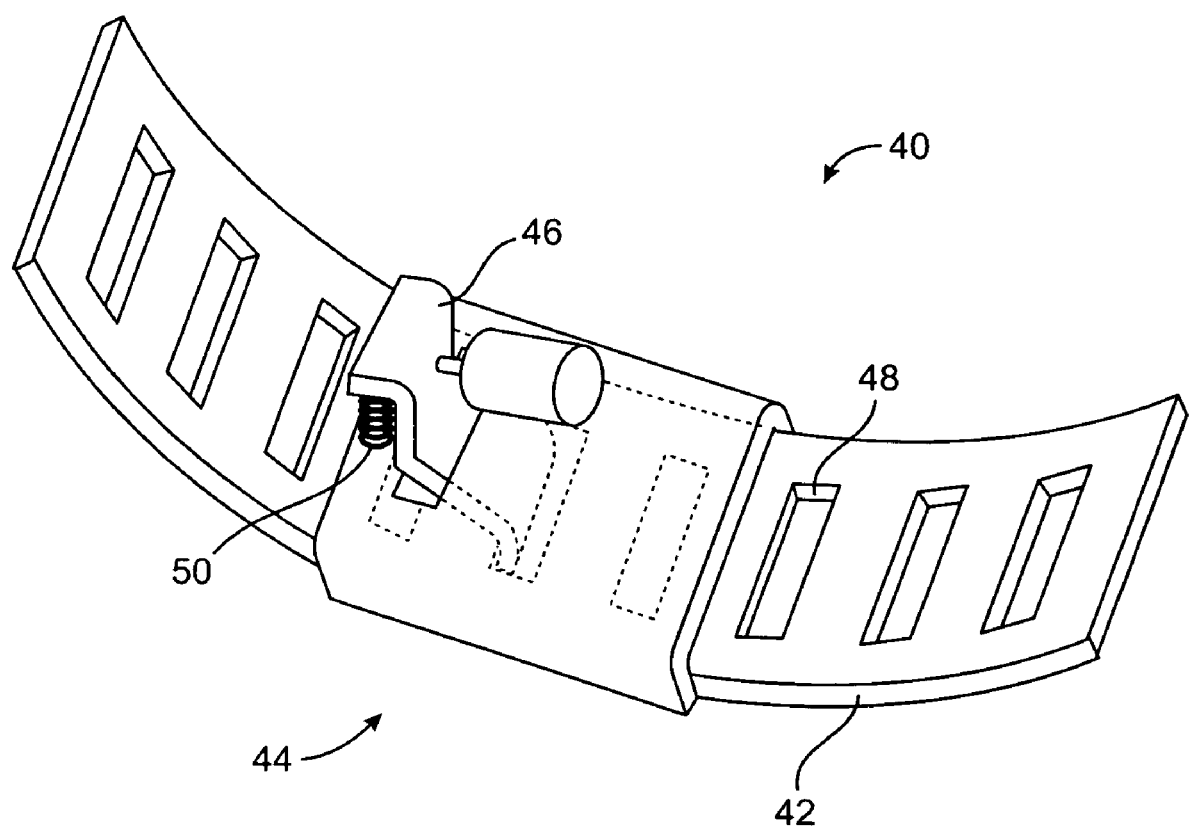
FIG. 5 is a close up view of a ring diameter adjustment mechanism for the atraumatic tissue retraction device.

If desired, the ring may be adjustable. The adjustability of the ring may be created in any suitable manner. FIG. 5 shows an embodiment of the retractor 40 that uses a ratchet type mechanism 44 to allow the user to expand the ring 42 once the ring 42 is in place. In this embodiment, the retractor 40 would be supplied to the user in a collapsed state and expanded once inserted into the chest cavity to anchor the retractor 40. The expansion would occur by the user mechanically increasing the diameter of the opening and ring 42 by hand or with one or more instruments. A spring-loaded locking lever 46 would be biased toward the ring 42 surface and holes 48 extending into or through the ring 42. The configuration of the locking lever 46 would allow the lever 46 to easily rise out of the holes 48 while the ring 42 is being expanded, but would be held securely in place inhibiting the ring 42 from collapsing. For the purposes of releasing the ring 42 to remove the retractor 40 after surgery, the spring 50 that biases the lever 46 toward the holes 48 would be compressed to allow the end of the lever 46 to pull out of the hole 48, and thereby allowing the ring 42 to collapse. Alternately, a shape memory alloy could be used. The function of this alloy would be to hold the ring in its expanded state when at room temperature, and then to release the ring when it's temperature is elevated. Alternately, a component that is able to be severed by an electrosurgery probe or other surgical instrument could be used to hold the ring in its expanded state. In this case, the support component would be severed to allow the ring to collapse.

Alternate versions of the adjustable ring also may be used. One version could use a mechanical stop that is actuated by hydraulic means to hold the ring in its expanded state. A piston could be actuated by hydraulic or mechanical mechanisms. Or a threaded member could be twisted to expand or contract the ring.

Figure 6:
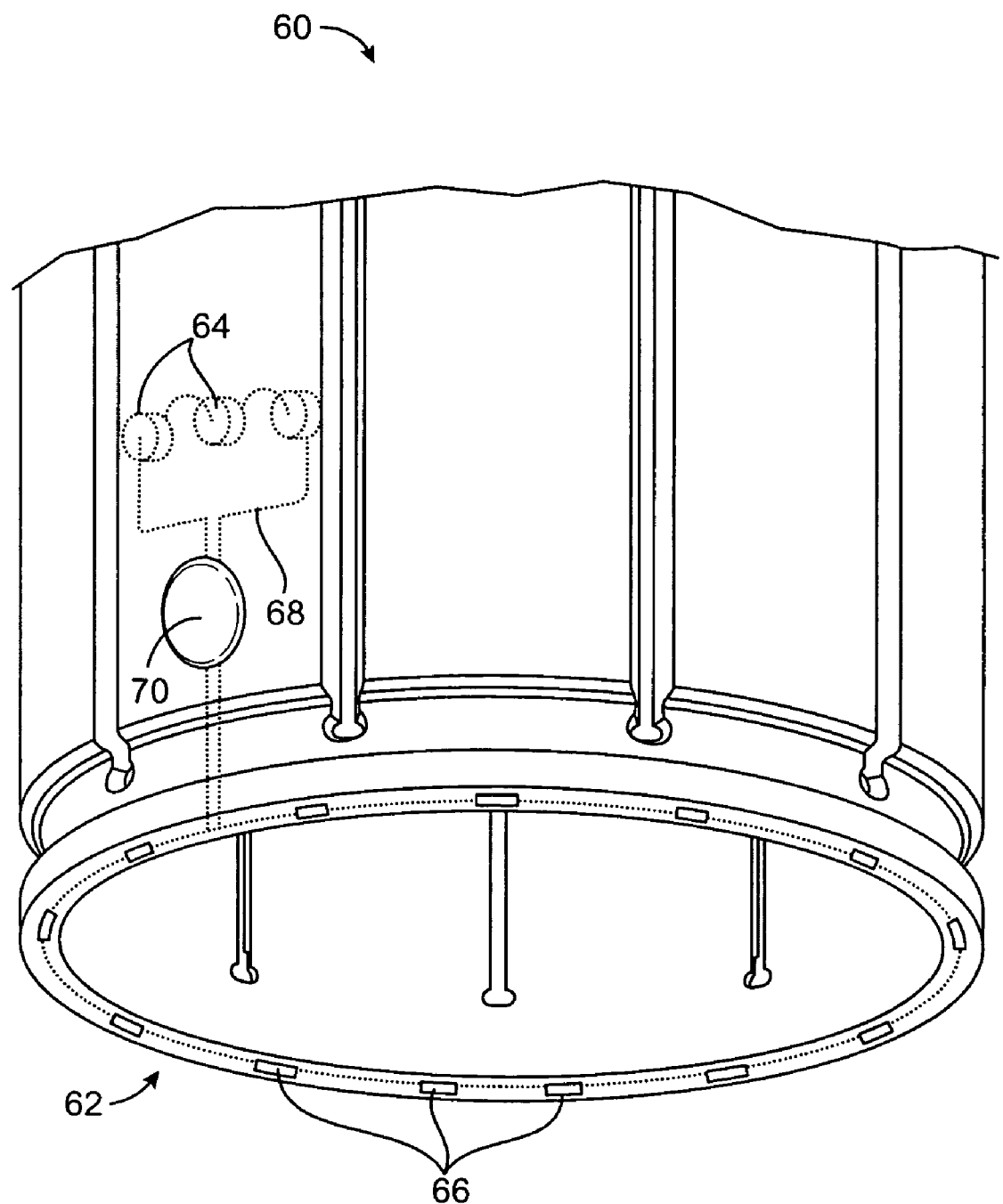
FIG. 6 is a close up view of lighting integrally molded into the base of the atraumatic tissue retraction device.

Additionally, the distal end of the device 60 can be outfitted with a light source 62 for the purposes of illuminating the surgical site. The light 62 may take the form of an accessory that is attachable to the retractor or it may be integrally formed with the retractor 60. FIG. 6 shows a retractor 60 having a series of batteries 64 molded into silicone in one or more of the straps 16. A series of LED's 66 are also molded into the silicone around the distal ring 14. Leads 68 connect the LED's 66 and batteries 64 to a switch 70, such as a push button contact switch or other suitable switch, which allows the user to turn the light source 62 on and off.

Another embodiment of the retractor 78 has an inflatable, adjustable or malleable flange extending from the bottom of the ring, as seen in FIG. 7. Initially, the malleable flange 82 would extend down from the ring 14. Once the retractor 78 has been lowered into place, the flange 82 could be bent outward to help anchor the retractor 78 in place. The flange 82 could be bent only slightly or it may be bent such that it is fully perpendicular or further. The flange 82 may be bent to conform to the shape of the chest wall, ribs or other structure. Stainless steel is a suitable material, although any biocompatible or coated malleable material maybe used. This embodiment of the retractor 78 also shows adhesive patches 84 used to connect the straps 16 directly to the support surface. The adhesive patches 84 have a disposable peel off backing 86 to protect the adhesive prior to use.

The retractor may be supplied as a sterile, single use device or a reusable device formed of materials suitable for sterilization procedures.

Many features have been listed with particular configurations, options, and embodiments. Any one or more of the features described may be added to or combined with any of the other embodiments or other standard devices to create alternate combinations and embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention as set forth in the following claims.

What is claimed is:

1. A surgical retractor to allow improved access through a surgical opening through the tissue of a patient, comprising:
    a ring,
        a plurality of flexible straps, each strap having a proximal end, a distal end, a first lateral side and a second lateral side, said distal end of said plurality of flexible straps connected to said ring,
        a connector attached to each of said plurality of straps, said connector capable of connecting said strap to a support surface,
        a malleable flange extending distally from said ring,
        said surgical retractor having an initial position wherein the first lateral side of each flexible strap is connected to the second lateral side of an adjacent flexible strap, thus forming an elongated sleeve structure, and
        said surgical retractor having a deployed position wherein at least a portion of the first lateral side of each flexible strap is disconnected from the second lateral side of the adjacent flexible strap,
        wherein, when the surgical retractor is in the deployed position, a proximal portion of the first lateral side of each flexible strap is disconnected from the second lateral side of the adjacent flexible strap and a distal portion of the first lateral side of each flexible strap remains connected to the second lateral side of the adjacent flexible strap forming a distal sleeve structure.

2. The surgical retractor of claim 1, wherein said support surface is chosen from the group of support surfaces including a patient's skin, a surgical drape and a piece of surgical equipment.

3. The surgical retractor of claim 1, wherein a diameter of said ring is adjustable.

4. The surgical retractor of claim 3, wherein adjustment of said ring is achieved with ratchet mechanism.

5. The surgical retractor of claim 1, wherein said plurality of straps are formed of a silicone material.

6. The surgical retractor of claim 1, further comprising a light source molded into said ring.

7. The surgical retractor of claim 6, wherein said light source is a plurality of LEDs.

8. The surgical retractor of claim 1, further comprising an inflatable bladder forming at least a portion of said ring.

9. The surgical retractor of claim 8, further comprising a pneumatic line attached to said inflatable bladder.

10. The surgical retractor of claim 1, wherein said plurality of flexible straps is at least 6 straps.

11. The surgical retractor of claim 1, wherein said ring is approximately round.

12. The surgical retractor of claim 1, wherein said malleable flange has an initial position extending downward from said ring and a deployed position bent outward from said ring.

13. The surgical retractor of claim 1, wherein said ring is flexible.

14. The surgical retractor of claim 1, wherein said ring is formed of a shape memory alloy.

15. The surgical retractor of claim 1, wherein said connector is formed of an adhesive patch.

16. The surgical retractor of claim 1, wherein said connector is formed of a patch of hook or loop material connected to a surface of each of said plurality of straps and a coordinating patch of hook or loop material connectable to a support surface.

17. The surgical retractor of claim 1, wherein, when the surgical retractor is in the deployed position, the first lateral side of each flexible strap is completely disconnected from the second lateral side of the adjacent flexible strap.

18. A surgical retractor to allow improved access through a surgical opening through the tissue of a patient, comprising:
    a ring,
        a plurality of flexible straps, each strap having a proximal end, a distal end, a first lateral side and a second lateral side, said distal end of said plurality of flexible straps connected to said ring,
        a connector attached to each of said plurality of straps, said connector capable of connecting said strap to a support surface,
        said surgical retractor having an initial position wherein the first lateral side of each flexible strap is connected to the second lateral side of an adjacent flexible strap, thus forming an elongated sleeve structure, and
        said surgical retractor having a deployed position wherein at least a portion of the first lateral side of each flexible strap is disconnected from the second lateral side of the adjacent flexible strap,
    wherein, when the surgical retractor is in the deployed position, a proximal portion of the first lateral side of each flexible strap is disconnected from the second lateral side of the adjacent flexible strap and a distal portion of the first lateral side of each flexible strap remains connected to the second lateral side of the adjacent flexible strap forming a distal sleeve structure;
    wherein a diameter of said ring is adjustable, and wherein adjustment of said ring is achieved with a spring loaded ratchet mechanism, including:
        a plurality of openings extending into said ring,
        an arm having an end sized and configured to extend into said plurality of openings, said arm having an engaged position wherein said end of said arm is located within one of said plurality of openings and a released position wherein said end of said arm is outside all of said plurality of openings, and a spring configured to bias said arm towards said engaged position.

19. A surgical retractor to allow improved access through a surgical opening through the tissue of a patient, comprising:
a ring,
a plurality of flexible straps, each strap having a proximal end, a distal end, a first lateral side and a second lateral side, said distal end of said plurality of flexible straps connected to said ring,
a connector attached to each of said plurality of straps, said connector capable of connecting said strap to a support surface,
said surgical retractor having an initial position wherein the first lateral side of each flexible strap is connected to the second lateral side of an adjacent flexible strap, thus forming an elongated sleeve structure, and
said surgical retractor having a deployed position wherein at least a portion of the first lateral side of each flexible strap is disconnected from the second lateral side of the adjacent flexible strap,
wherein, when the surgical retractor is in the deployed position, a proximal portion of the first lateral side of each flexible strap is disconnected from the second lateral side of the adjacent flexible strap and a distal portion of the first lateral side of each flexible strap remains connected to the second lateral side of the adjacent flexible strap forming a distal sleeve structure;
wherein each of said flexible straps is frangibly connected into an adjacent one of said plurality of flexible straps.

20. The surgical retractor of claim 19, wherein the frangible connection is created by a narrowed portion of the strap material.

21. The surgical retractor of claim 19, wherein the frangible connection is along the length of each of the straps.

22. The surgical retractor of claim 19, wherein the frangible connection is at a discrete point.

23. A method of using a surgical retractor in a surgical incision, the method comprising the steps of:
(a) inserting a distal end of the surgical retractor into the surgical incision, the surgical retractor being configured as an elongated sleeve structure having a proximal end and a distal end, a ring connected to said distal end of said sleeve structure, and a malleable flange extending distally from said ring;
(b) causing the ring located on the distal end of the surgical retractor to open to a deployed configuration;
(c) separating said sleeve structure into a plurality of flexible straps along a proximal portion of said sleeve structure, leaving a distal portion of said sleeve structure in a sleeve configuration;
(d) placing tension on said plurality of straps to retract the surgical incision;
(e) bending said malleable flange outwardly from said ring.

24. The method of claim 23, further comprising the steps of:
(e) performing a surgical procedure through a passageway through the surgical retractor.

25. The method of claim 24, wherein said surgical procedure is selected from the group of procedures including CABG, valve repair, valve replacement and ablation.

26. The method of claim 23, wherein said straps are stretched during step (d), thereby providing additional force against tissues forming an edge of the surgical incision.

27. The method of claim 23, wherein said first and second parts of said coordinating fastener are hook and loop fastener and further comprising the step of repositioning said second part of said coordinating fastener.

28. The method of claim 23, wherein step (b) is performed by inflating an inflatable bladder which forms said ring.

29. The method of claim 23, wherein in step (d) the straps are pulled different amounts to create a non-round passageway.

30. The method of claim 23, wherein in step (d) the straps are pulled approximately the same amount to create a generally round passageway.

31. The method of claim 23, wherein step (b) includes increasing the diameter of the ring.

32. The method of claim 23, further comprising:
(e) placing a plurality of a first part of a coordinating fastener around the surgical incision;
(f) connecting a second part of said coordinating fastener located on said plurality of straps to said first part of said coordinating fastener.

33. A method of using a surgical retractor in a surgical incision, the method comprising the steps of:
(a) inserting a distal end of the surgical retractor into the surgical incision, the surgical retractor being configured as an elongated sleeve structure having a proximal end and a distal end, and a ring connected to said distal end of said sleeve structure;
(b) causing the ring located on the distal end of the surgical retractor to open to a deployed configuration;
(c) separating said sleeve structure into a plurality of flexible straps along a proximal portion of said sleeve structure, leaving a distal portion of said sleeve structure in a sleeve configuration;
(d) placing tension on said plurality of straps to retract the surgical incision;
wherein said surgical procedure is a cardiac ablation procedure and said surgical retractor is used in a first thoracic incision and a second surgical retractor is used in a second thoracic incision, said second thoracic incision being located on an opposite side of the sternum from said first thoracic incision.

34. A method of using a surgical retractor in a surgical incision, the method comprising the steps of:
(a) inserting a distal end of the surgical retractor into the surgical incision, the surgical retractor being configured as an elongated sleeve structure having a proximal end and a distal end, and a ring connected to said distal end of said sleeve structure;
(b) causing the ring located on the distal end of the surgical retractor to open to a deployed configuration;
(c) separating said sleeve structure into a plurality of flexible straps along a proximal portion of said sleeve structure, leaving a distal portion of said sleeve structure in a sleeve configuration;
(d) placing tension on said plurality of straps to retract the surgical incision;
wherein in step (c) said sleeve structure is separated into said plurality of flexible straps along an entire length of said sleeve structure.

35. A surgical retractor to allow improved access through a surgical opening through the tissue of a patient, comprising:
a ring,
an elongated sleeve structure having a proximal end and a distal end, said distal end of said sleeve structure connected to said ring,
said sleeve structure being separable into a plurality of flexible straps, a connector attached to each of said plurality of straps, said connector capable of connecting said strap to a support surface, and a malleable flange extending distally from said ring.

36. The surgical retractor of claim 35, wherein, when the surgical retractor is in a deployed position, said sleeve structure is separated into said plurality of flexible straps along an entire length of said sleeve structure.

37. The surgical retractor of claim 35, wherein, when the surgical retractor is in a deployed position, said sleeve structure is separated into said plurality of flexible straps along a proximal portion of said sleeve structure, leaving a distal portion of said sleeve structure in a sleeve configuration.

38. The surgical retractor of claim 35, wherein a diameter of said ring is adjustable.

39. The surgical retractor of claim 38, wherein adjustment of said ring is achieved with ratchet mechanism.

40. The surgical retractor of claim 38, wherein adjustment of said ring is achieved with a spring loaded ratchet mechanism, including:
    a plurality of openings extending into said ring,
    an arm having an end sized and configured to extend into said plurality of openings, said arm having an engaged position wherein said end of said arm is located within one of said plurality of openings and a released position wherein said end of said arm is outside all of said plurality of openings,
    and a spring configured to bias said arm towards said engaged position.

41. The surgical retractor of claim 35, wherein said sleeve structure comprises a plurality of frangible connections allowing said sleeve structure to be separated into said plurality of flexible straps.

42. The surgical retractor of claim 41, wherein each frangible connection is created by a narrowed portion of the sleeve structure material.

43. The surgical retractor of claim 41, wherein said plurality of frangible connections extend along an entire length of said sleeve structure.

44. The surgical retractor of claim 41, wherein said plurality of frangible connections extend along a portion of a length of said sleeve structure.

45. The surgical retractor of claim 41, wherein each frangible connection is at a discrete point.

46. The surgical retractor of claim 35, wherein said sleeve structure is formed of a silicone material.

47. The surgical retractor of claim 35, further comprising a light source molded into said ring.

48. The surgical retractor of claim 47, wherein said light source is a plurality of LEDs.

49. The surgical retractor of claim 35, further comprising an inflatable bladder forming at least a portion of said ring.

50. The surgical retractor of claim 49, further comprising a pneumatic line attached to said inflatable bladder.

51. The surgical retractor of claim 35, wherein said plurality of flexible straps is at least 6 straps.

52. The surgical retractor of claim 35, wherein said ring is approximately circular.

53. The surgical retractor of claim 35, wherein said ring is flexible.

54. The surgical retractor of claim 35, wherein said ring is formed of a shape memory alloy.

55. The surgical retractor of claim 35, wherein said connector is formed of an adhesive patch.

56. The surgical retractor of claim 35, wherein said connector is formed of a patch of hook or loop material connected to a surface of each of said plurality of straps and a coordinating patch of hook or loop material connectable to a support surface.

57. A surgical retractor to allow improved access through a surgical opening through the tissue of a patient, comprising:
    a ring,
        a plurality of flexible straps, each strap having a proximal end, a distal end, a first lateral side and a second lateral side, said distal end of said plurality of flexible straps connected to said ring,
        a connector attached to each of said plurality of straps, said connector capable of connecting said strap to a support surface,
        said surgical retractor having an initial position wherein the first lateral side of each flexible strap is connected to the second lateral side of an adjacent flexible strap, thus forming an elongated sleeve structure, and
        said surgical retractor having a deployed position wherein at least a portion of the first lateral side of each flexible strap is disconnected from the second lateral side of the adjacent flexible strap,
and a malleable flange extending distally from said ring.

58. A method of using a surgical retractor in a surgical incision, the method comprising the steps of:
    (a) inserting a distal end of the surgical retractor into the surgical incision, the surgical retractor being configured as an elongated sleeve structure having a proximal end and a distal end, a ring connected to said distal end of said sleeve structure, and a malleable flange extending distally from said ring;
    (b) causing the ring located on the distal end of the surgical retractor to open to a deployed configuration;
    (c) separating said sleeve structure into a plurality of flexible straps;
    (d) placing tension on said plurality of straps to retract the surgical incision,
    (e) bending a said malleable flange outwardly from said ring.

* * * * *